(12) United States Patent
Lendlein et al.

(10) Patent No.: US 8,158,143 B2
(45) Date of Patent: Apr. 17, 2012

(54) SYSTEMS FOR RELEASING ACTIVE INGREDIENTS, BASED ON BIODEGRADABLE OR BIOCOMPATIBLE POLYMERS WITH A SHAPE MEMORY EFFECT

(75) Inventors: Andreas Lendlein, Berlin (DE); Susi Steuer, Aachen (DE); Annika Tuleweit, Aachen (DE)

(73) Assignee: Helmholtz-Zentrum Geesthacht Zentrum fuer Material- und Kuestenforschung GmbH, Geesthacht (DE)

( * ) Notice: Subject to any disclaimer, the term of this patent is extended or adjusted under 35 U.S.C. 154(b) by 1204 days.

(21) Appl. No.: 10/520,782

(22) PCT Filed: Jul. 10, 2003

(86) PCT No.: PCT/EP03/07515
§ 371 (c)(1),
(2), (4) Date: Dec. 16, 2005

(87) PCT Pub. No.: WO2004/006885
PCT Pub. Date: Jan. 22, 2004

(65) Prior Publication Data
US 2006/0140999 A1     Jun. 29, 2006

Related U.S. Application Data

(60) Provisional application No. 60/395,167, filed on Jul. 10, 2002, provisional application No. 60/218,408, filed on Jul. 14, 2000, provisional application No. 60/218,760, filed on Jul. 17, 2000.

(51) Int. Cl.
*A61F 13/02* (2006.01)
(52) U.S. Cl. .................................... 424/426
(58) Field of Classification Search .................. None
See application file for complete search history.

(56) References Cited

U.S. PATENT DOCUMENTS
5,529,782 A    6/1996   Staab
(Continued)

FOREIGN PATENT DOCUMENTS
EP    0 415 671    3/1991
(Continued)

OTHER PUBLICATIONS

Heilmann, "Osmotically Powered Alzet Osmotic Minipump," *Therapeutic Systems Pattern-Specific Drug Delivery; Concept and Development* (Ferdinand Enke, ed.), pp. 111-113, Thieme: Verlag, Stuttgart, 1978.

*Primary Examiner* — Carlos Azpuru
(74) *Attorney, Agent, or Firm* — Sughrue Mion, PLLC

(57) ABSTRACT

A drug release system is disclosed comprising a laminate structure comprising at least one layer comprising a matrix made from a shape memory material and at least one drug dispersed in the matrix, and layers from a shape memory material not containing a drug and sandwiching the at least one layer comprising the drug(s) on both surfaces, wherein the shape memory material of the layers not containing a drug, after triggering of the shape memory effect, controls the release rate of the drug(s). Another embodiment comprises at least one drug, a reservoir for receiving the drug(s), and at least one of a coating and a membrane closing the reservoir, wherein one of a material for the reservoir and a material for the coating or membrane is made from a shape memory material and wherein the shape memory material, after triggering the shape memory effect, controls the rate of release of the drug(s).

11 Claims, 9 Drawing Sheets

U.S. PATENT DOCUMENTS

| | | | |
|---|---|---|---|
| 5,650,173 A | 7/1997 | Ramstack et al. | |
| 6,160,084 A | 12/2000 | Grablowitz et al. | |
| 6,281,262 B1 | 8/2001 | Shikinami | |
| 6,388,043 B1 * | 5/2002 | Langer et al. | 528/80 |
| 2001/0009982 A1 | 7/2001 | Ferrera et al. | |
| 2003/0153972 A1 | 8/2003 | Helmus | |

FOREIGN PATENT DOCUMENTS

| | | |
|---|---|---|
| EP | 0 422 693 | 4/1991 |
| EP | 1 000 958 | 5/2000 |
| WO | WO 99/42147 | 8/1999 |
| WO | WO 99/42528 | 8/1999 |
| WO | WO 99/62576 | 12/1999 |
| WO | WO 01/91822 | 12/2001 |
| WO | WO 02/41929 | 5/2002 |
| WO | WO 02/060498 | 8/2002 |
| WO | WO 03/017882 | 3/2003 |
| WO | WO 03/088818 | 10/2003 |

* cited by examiner

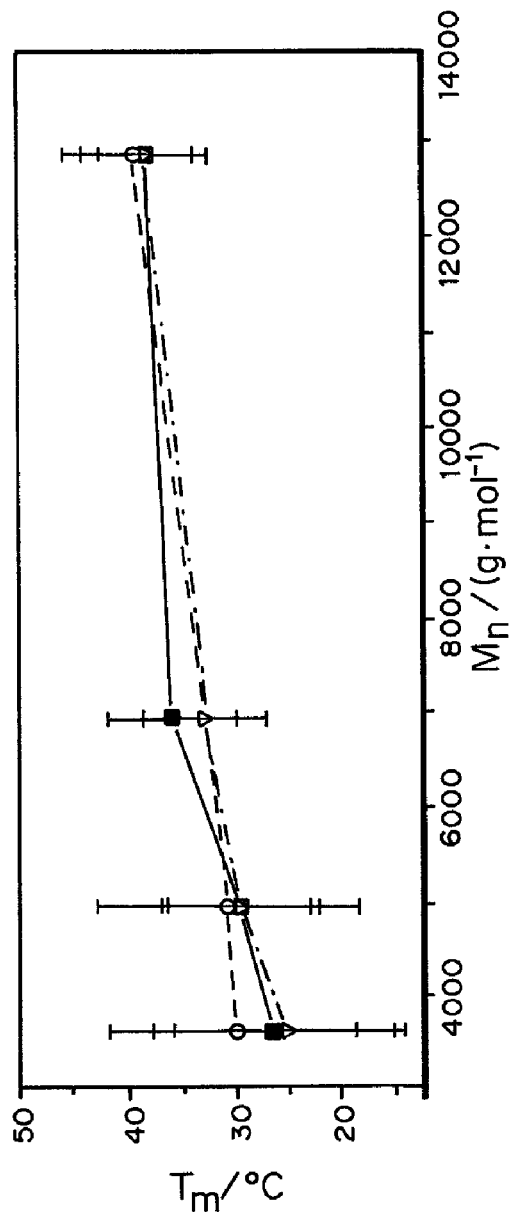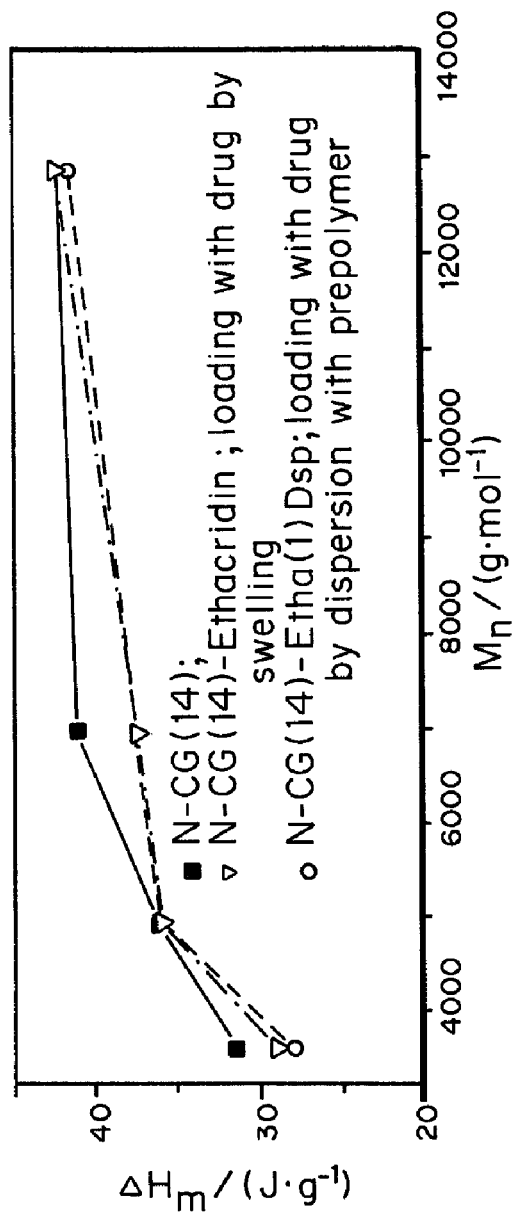
FIG. 2a
FIG. 2b

Seven-Layer
Triple-Layer unloaded Polymer

Polymer with
5% Gentamicin

SYSTEMS FOR RELEASING ACTIVE INGREDIENTS, BASED ON BIODEGRADABLE OR BIOCOMPATIBLE POLYMERS WITH A SHAPE MEMORY EFFECT

This application is a §371 filing of PCT/EP2003/007515, filed Jul. 10, 2003, which claims priority to U.S.S.N. 60/395,167 filed Jul. 10, 2002, U.S.S.N. 60/218,408 filed Jul. 14, 2002, and U.S.S.N. 60/218,760 filed Jul. 17, 2002.

The present invention relates to drug release systems on the basis of biodegradable or biocompatible polymers showing shape-memory-effects, to methods for the preparation of the drug release systems and to polymers showing shape-memory-effects, which are suitable for the preparation of the drug release systems.

PRIOR ART

Drug release systems, allowing a controlled release of enclosed drugs (active agents) at the desired target are since long subject of research. Since the common administration of active agents is associated with short-term high concentrations of the active agents, which subsequently decrease continuously, toxic concentrations of active agents often occur in combination with undesired side effects as well as non-effective concentrations without the desired activity. This has lead to the development of a number of polymeric release systems, which offer the possibility to increase the safety as well as the efficiency of the release of the drug by means of controlled release over a defined time period.

Such systems, which are in part already available on the market, however do show various drawbacks. Biostable implants for example have to be removed after release of the drug by means of a second surgical procedure. Known degradable systems on the other hand do have the tendency to show an undesired change with respect to the mechanical strength during release, since the mechanical properties sometimes often decrease sharply even during an early stage of the degradation.

Conventional drug release systems furthermore do show the drawback that large volume implants can only be administered using complex procedures, which is in particular true for implants which shall act at the same time as drug release systems. In this connection implants would be beneficial which allow a less complex procedure for their introduction into the body, with or without additional means for influencing the drug release.

OBJECT OF THE PRESENT INVENTION

Accordingly, it is the object of the present invention to provide drug release systems, which overcome the above-mentioned drawbacks of the prior art at least partly. In this connection at least one of the following achievements should be obtained:
1. A control of the release of the active agent (release) is possible on demand.
2. Large volume implants may be administered by means of minimal invasive procedures.

The drug release systems in accordance with the present invention preferably do release the enclosed active agent (drug), according to the need, either evenly over a defined period of time or controlled after having been subjected to an external stimulus.

SHORT DESCRIPTION OF THE PRESENT INVENTION

This object is solved with the drug release system according to claim 1. Preferred embodiments of the system are defined in the sub claims. Furthermore the present invention provides a method for the preparation of drug release systems, as well as polymeric materials, suitable for use in the drug release systems.

SHORT DESCRIPTION OF THE FIGURES

FIG. 2 shows the influence of the loading with active agent on the thermal properties of networks of caprolactone-co-glycolide of different segment lengths.

Figure 6:
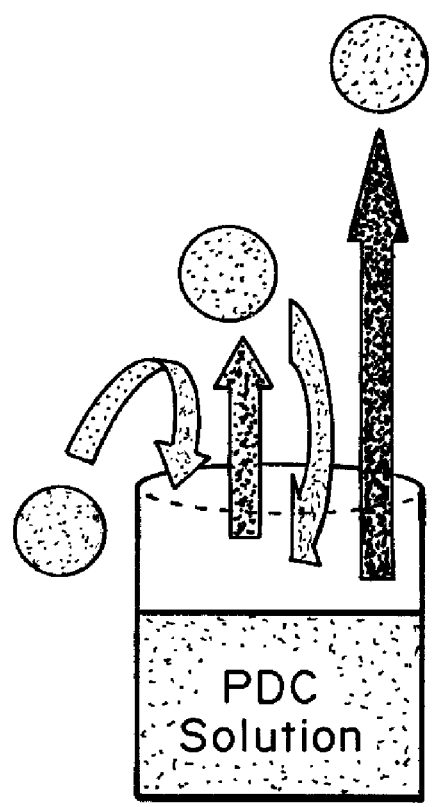

FIG. 6 schematically discloses the dip-coating method for the modification of the drug release systems.

Figure 7:
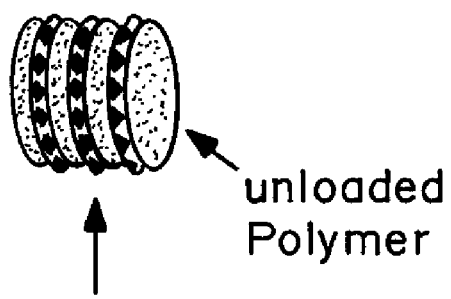

FIG. 7 discloses the structure of layer systems.

Figure 8:
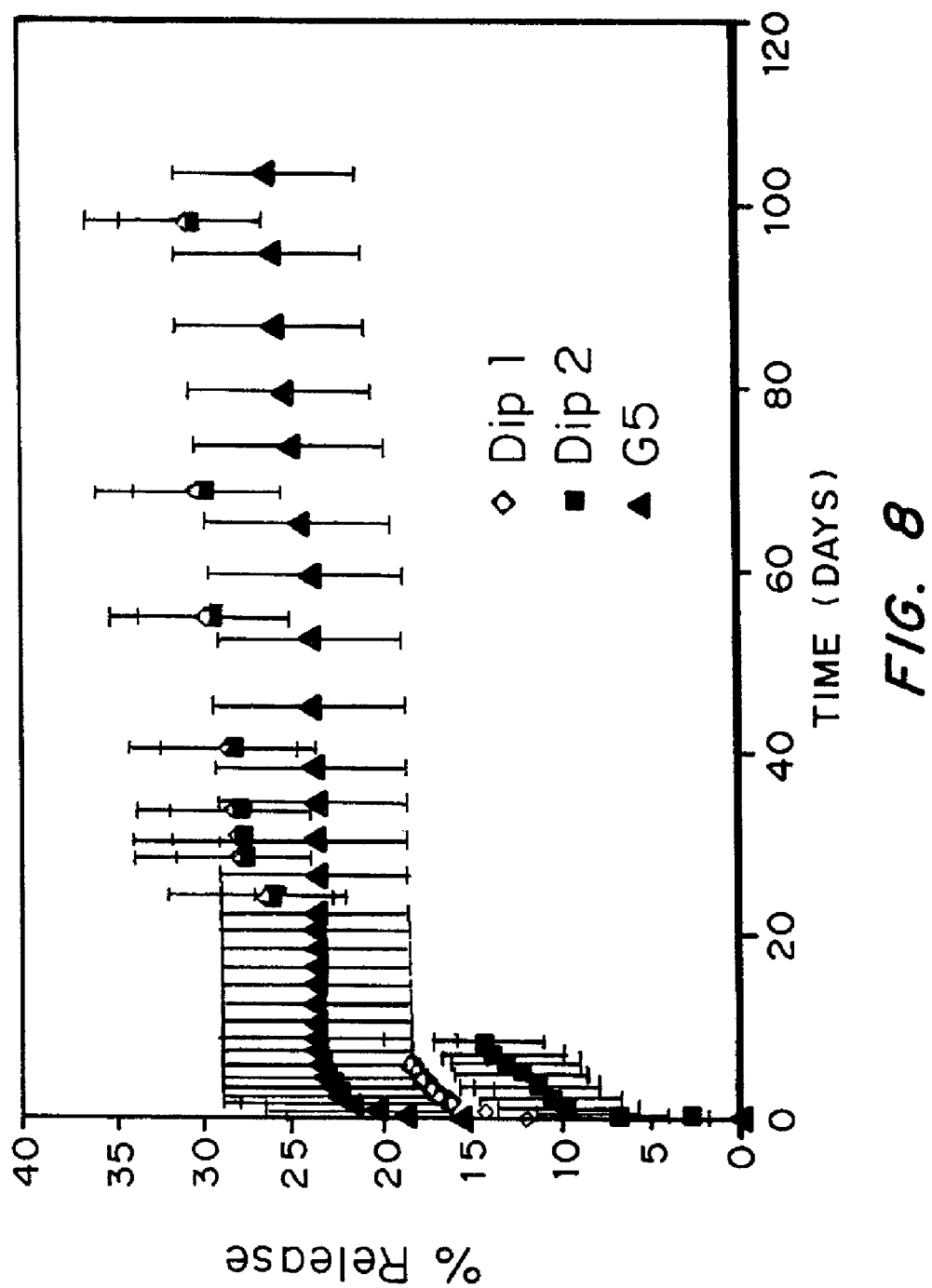

FIG. 8 shows the modification of the release of gentamicine (G5) by means of dip coating.

Figure 9:
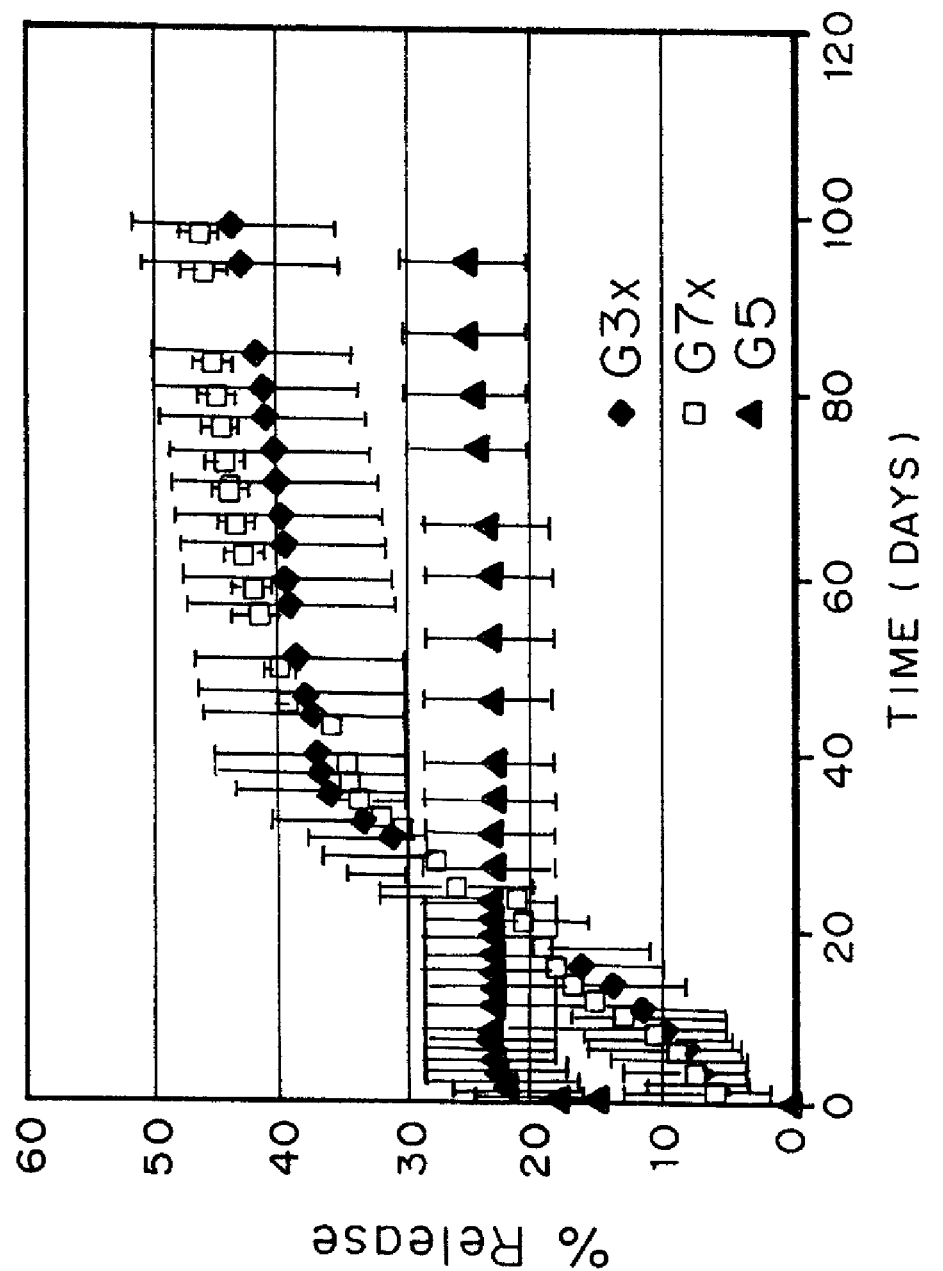
Figure 10A:
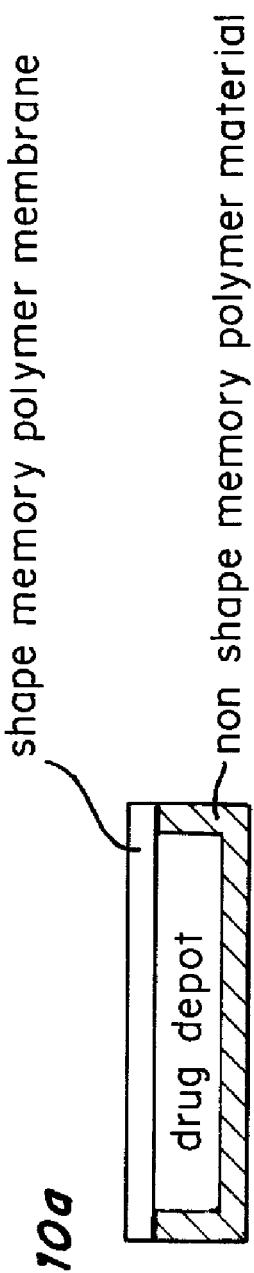
Figure 10B:
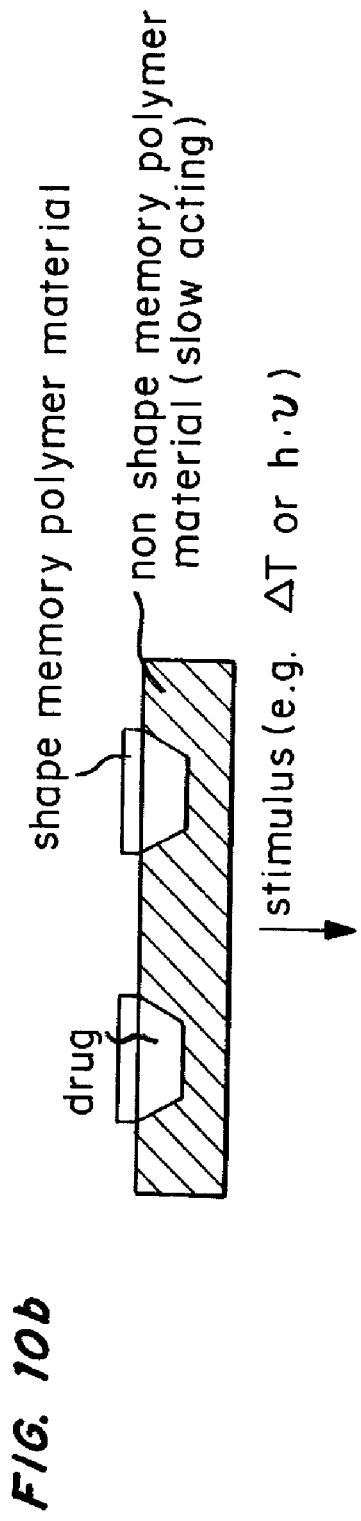
Figure 10C:
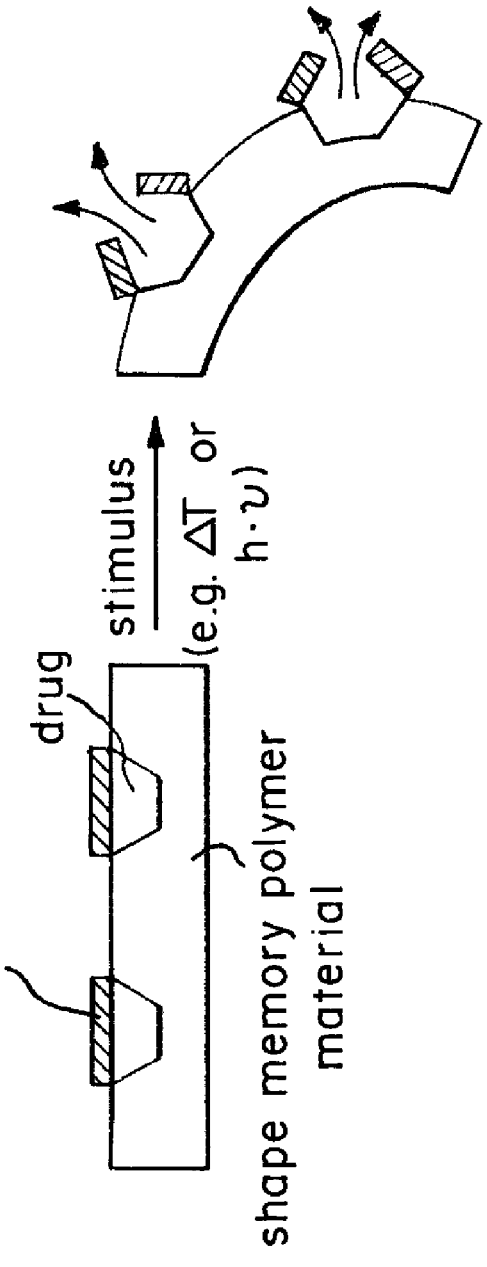
Figure 10D:
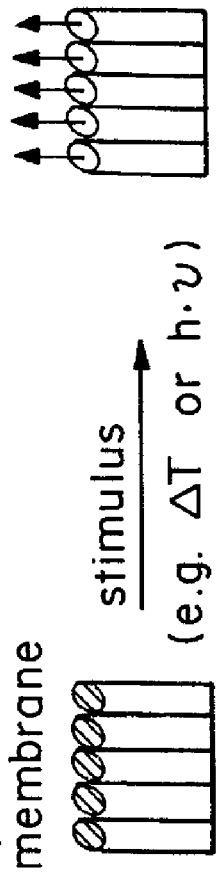

FIG. 9 shows the modification of the release of gentamicine (G5) by means of layer systems.

FIG. 10 shows different schematic descriptions of drug release systems in accordance with the present invention.

Figure 1:
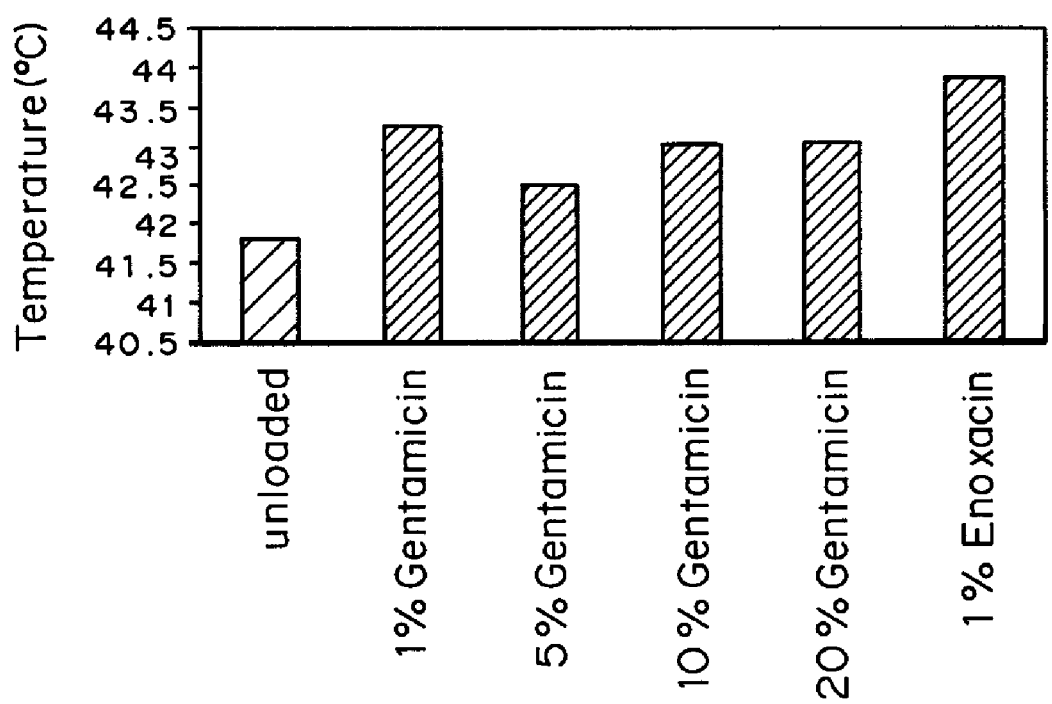
FIG. 1 shows the influence of the loading with active agent on the melting temperature of a multi block copolymer of paradioxanone segments and caprolactone segments.

The loading of a multi block copolymer, based on paradioxanone units and caprolactone units, with drugs of different polarity and in different concentrations does not show a significant influence on the melting temperature of the triggering segment, i.e. the temperature of the shape memory transition is not substantially changed (FIG. 1). The loading of polyurethane networks, based on lactide-co-glycolide segments with drugs of different polarity in a concentration of 1 wt. % as well does not have any influence on the glass transition temperature, i.e. the shape memory transition remains unchanged. A similar result has been shown for networks of caprolactone-co-glycolide segments of differing segment lengths, loaded with ethacridine lactate (FIG. 2).

Drug Release

Figure 3:
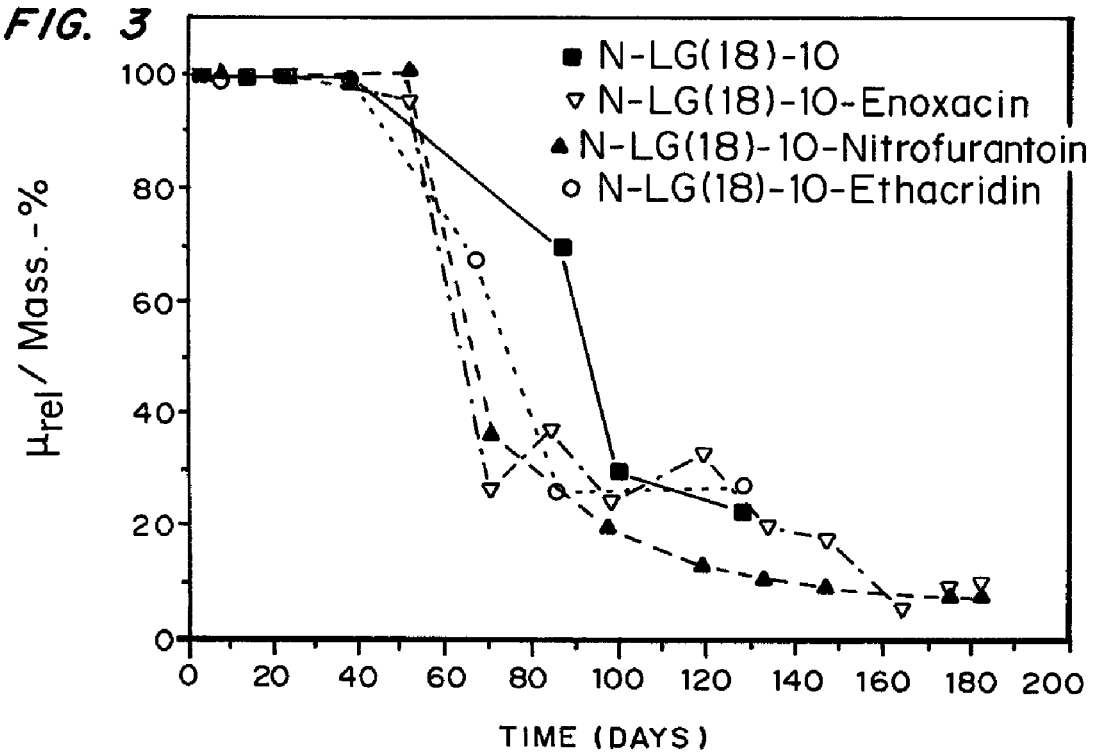
FIG. 3 shows the degradation behaviour of amorphous, active agent containing networks.
Figure 4:
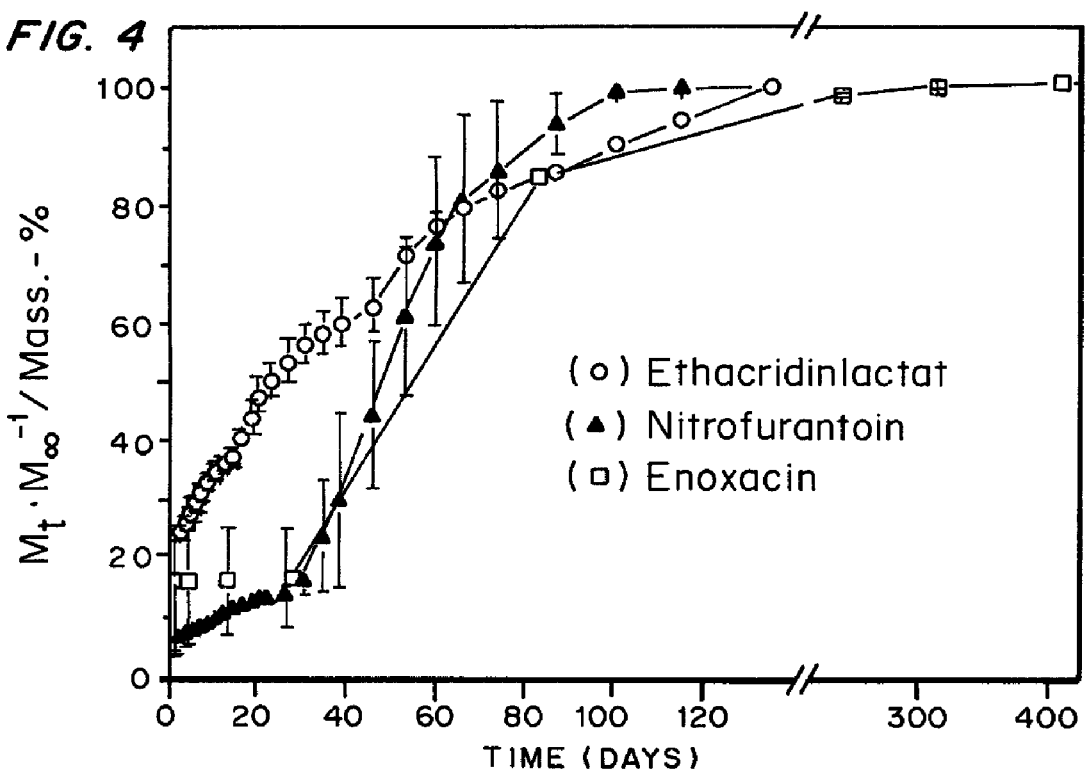
FIG. 4 shows the drug release from amorphous networks.
Figure 5:
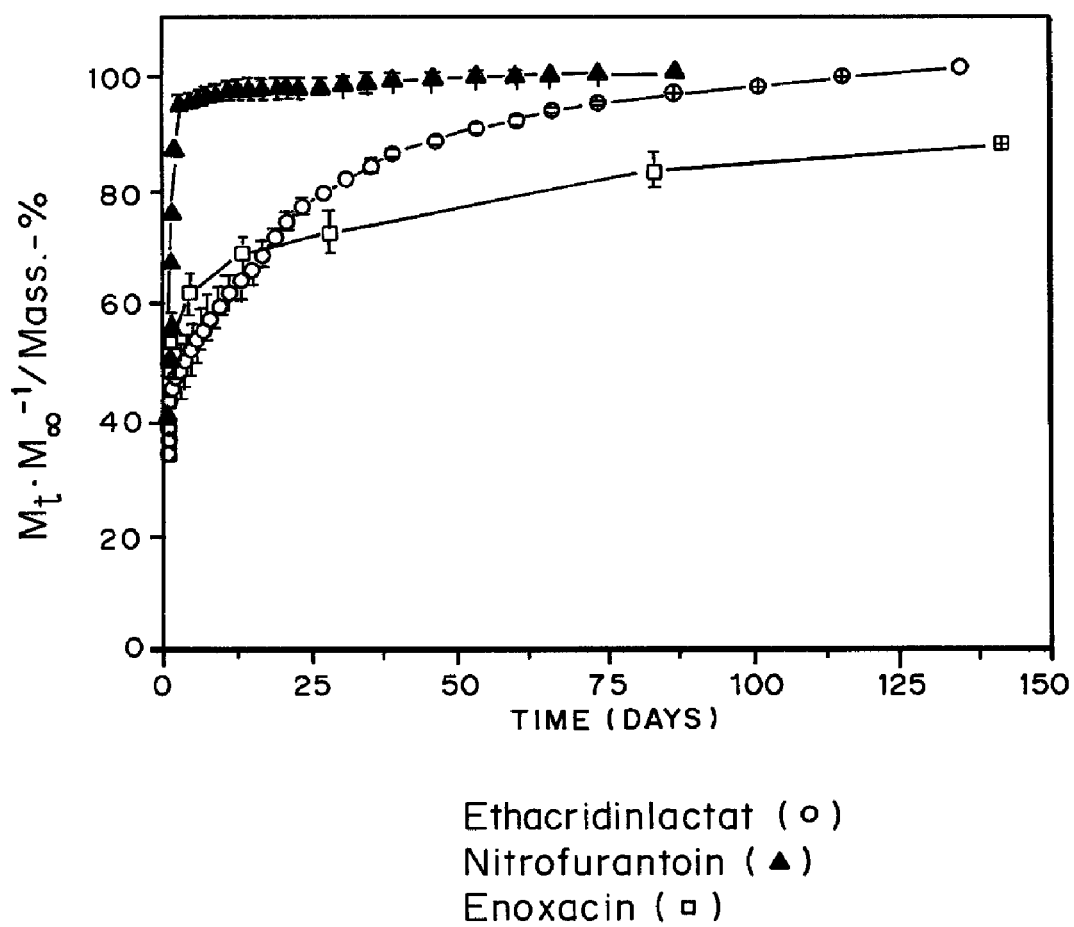
FIG. 5 shows the drug release from crystalline networks.

FIG. 3 shows that the mass loss of the networks only starts after a degradation time of about 50 days. With respect to the release of drugs this implies that within the first 50 days the release is controlled by means of diffusion, whereas after the first 50 days the drug release is associated with the degradation of the matrix. The drug release from an amorphous matrix N-LG(18)-10, for loadings with nitrofurantoine and enoxancine, shows a step profile, which is typical for copolymer matrix systems comprising lactate and glycolate (FIG. 4). The more hydrophilic drug ethacridine lactate, compared to nitrofuantoine and enoxacine, is released more rapidly. At the beginning of the release often a burst-effect can be seen, based on the release of drugs being adhered to the surface. The second interval is characterized by means of the diffusion-controlled release of the substance from the matrix to the surface of the matrix. With ongoing release the remaining content of drug is released in association with a rapid polymer erosion (see FIG. 3). This effect is designated in the literature as well as dose dumping.

The drug release can be optimized by means of dip coating (FIG. 6) or by means of the preparation of layer systems (FIG. 7).

With multi block copolymers based on paradioxanone and caprolactone a burst release can be seen at the beginning of the release, and a plateau is reached within 2 days. A modification can be obtained by means of dip coating using the matrix polymer or by means of preparation of layer systems, wherein a film containing the active agent is sandwiched between films of pure polymer. Thereby the initial burst can be avoided and, in the case of layer systems, a linear release can be achieved which lasts for several weeks (FIG. 8 and FIG. 9).

DETAILED DESCRIPTION OF THE PRESENT INVENTION

The above-mentioned aim of the control of the drug release on demand can be obtained when a change with respect to the diffusion property can be initiated by means of use of an external stimulus. Such drug release systems can be designed, in accordance with the present invention, as follows (see also FIG. 10):

1. The drug is provided within a depot, which is closed with a membrane. Either the membrane or the depot (or both) comprises a shape memory polymer material.
2. The drug is present in dispersed form, i.e. either dissolved or encapsulated, within a matrix of shape memory polymer material. This matrix optionally can be provided with a coating or the matrix as such restricts the release of the drug.
3. Different drugs are provided in different depots or different domains of the matrix or are provided in different matrix systems. The depots each may be closed by means of membranes, which may be different.

The release can be obtained by means of the following options:

1. In systems, wherein the drug is enclosed within a depot (which preferably does not consist of a shape memory polymer material), closed by means of a membrane made from a shape memory polymer material, the release can be initiated by means of triggering the shape memory effect, whereby the status of the membrane is changed, from non-permeable with respect to the drug to permeable (either by means of a destruction of the membrane or by means of a change with respect to the permeability, by means of a change of the pore structure or the crystallinity; asymmetric membranes are a further option). With systems comprising several depots with differing drugs, the shape memory effect can as well be used for the release. Are the different depots closed by means or membranes made from differing shape memory polymer materials, which are not influenced by means of the same stimulus, a time dependent harmonized order of release can be obtained.
2. Alternatively it is possible to provide depot systems wherein the support (i.e. the depot material) is made from a shape memory polymer material or contains a shape memory polymer material. Upon triggering of the shape memory effect the associated change with respect to the shape destroys the membranes which close the depots, enabling a release.
3. In matrix systems the triggering of the shape memory effect may influence the release property, for example by means of a change concerning the crystallinity, the pore structure or else.
4. With all of the above named systems it is also possible to control the release properties by means of degradation of the shape memory polymer material.

With all systems comprising shape memory polymer materials, it is possible to trigger the shape memory effect by means of a suitable stimulus, such as temperature, light (radiation) or a combination thereof. As already disclosed above, the drug release systems may comprise different shape memory polymer materials, which may be receptive to different stimuli.

When the shape memory effect is not required for the control of the drug release, it is possible to use this effect for the preparation of implants which may be administered using minimal invasive techniques. In this connection, a drug release system is loaded with the drug and is brought into a shape which allows a minimal invasive implantation, wherein this shape, with respect to the shape memory polymer material, corresponds to the temporary shape. After the implantation the shape memory effect is triggered (see above) and the implant is brought into the permanent shape (with respect to the shape memory properties), which is in these cases usually a more voluminous form, compared with the temporary shape.

The term drug or active agent as used in accordance with the present invention shall be interpreted broadly. This term shall designate chemical as well as biological substances or mixtures, which can be thought of as being drugs in the broadest sense. In particular comprised are substances or mixtures having a medicinal activity, as medicament as well however as diagnostic agent or contrast agent. Furthermore, cosmetically active agents and mixtures shall be comprised, as well as auxiliary agents, such as artificial tears or else. The drugs to be used in accordance with the present invention may be of low molecular weight or they may be of high molecular weight (for example proteins).

The term drug release system, as employed in accordance with the present invention, comprises the two principle types of systems already mentioned above.

The first principle type comprises a matrix, within which the drug, which is to be released, is present in dispersed form. Such systems are used in particular in the form of implants for the release of drugs over a prolonged period of time. In this connection, it has been established in accordance with the present invention that loadings of 1 to 25 wt. % of drug are possible, without exerting a detrimental effect on the shape memory properties.

The second principle type has a more complex design and comprises a depot containing the drug and as well a construction which controls the release, for example a membrane surrounding the depot of the drug or an osmotic pump system (see in particular K. Heilmann, Therapeutische Systeme, Ferdinand Enke Verlag, Stuttgart, 1882, as well as WO 99/62576).

The drug release systems in accordance with the present invention may be employed for a broad variety of indications, in particular however for the treatment and/or prophylaxis of disorders (diseases, allergies, post-operative trauma) which require a long duration of the release of active agent, in order to reduce pain, in order to support regeneration of tissue, in order to provide protection concerning infections or in order to act against infections.

In addition to the essential components of the drug release systems, described in the following, these drug release systems may comprise further components, such as coatings, additives, etc., which for example may be used in order to adjust the biocompatibility (tissue compatibility) or other properties, such as X-ray contrast, etc.

The present invention is characterized in that the shape memory polymers (in the following designated also SMP (shape memory polymer)) are comprised as essential components, i.e. either as essential component of the matrix (in connection with the first principle type of system) or as essential component of the membrane or the osmotic pump (in relation to the second principle type of systems). The use of SMP materials enables in this connection that the shape memory effect improves the drug release, as will be shown in the following.

Surprisingly it has been found that specific biodegradable or biocompatible polymers having shape memory properties are suitable as matrix materials for drug release systems and as components of the other drug release systems. The polymeric materials which may be employed in accordance with the present invention can be classified in principle into two classes, thermoplastic polymers on the one hand and thermoset polymers on the other hand.

In principle all SMP materials may be used, for example those disclosed in the two International applications WO 99/42528 and WO 99/42147. The disclosures of these two applications are incorporated herein by reference. Such materials may be present in the form of thermoplastic materials or in the form of network materials. These shape memory polymers, which may be used in the present invention, may possess one but also two shapes in memory and these comprise at least one hard segment and at least one soft segment. The structure of the polymers is not restricted and suitable examples comprise linear polymers, graft polymers, dendrimeres, branched polymers, star shaped polymers (for thermoplastic materials) and semi-interpenetrating networks, interpenetrating networks, mixed interpenetrating networks and networks (thermoset materials).

These structures comprise typically segments derived from caprolactone, paradioxanone, lactide, glycolide or ethylene oxide oligomers or propylene oxide oligomers. In the case of the thermoplastic materials, the linkage between the different segments (oligomers/macro monomers) present in diol form, may be achieved by means of using a diisocyanate, for example TMDI. The network structures may be crosslinked in the form of segments having acrylate terminal groups, optionally using additional low molecular weight acrylates. If star-shaped macro monomers are employed, i.e. macro monomers having more than two terminals, a cross-linkage may be obtained also using OH-terminal groups, for example using diisocyanates, such as TMDI.

Preferred materials for the drug release systems in accordance with the present invention are however as follows:

The thermoplastic polymers which may be used in accordance with the present invention may be described as block copolymers, comprising at least one hard segment and at least one soft segment, wherein the hard segment comprises units derived from paradioxanone and wherein the soft segments comprises units derived from caprolactone and/or lactide and glycolide. The segments are preferably linked by means of urethane bonds. The segments each do have preferably a number average molecular weight of from 1000 to 10000 g/mol, in particular preferably from 3000 to 8000 g/mol. The linkage preferably is obtained by obtained by means of urethane bonds, obtained by means of a reaction of suitably functionalized segments with TMDI. The molecular weight of the resulting thermoplastic polymers is not critical and lies within the usual range for such SMP materials.

The thermoset materials which may be used in accordance with the present invention are networks, which may be semi-crystalline or amorphous. The preferred network which may be used in accordance with the present invention are polyurethane networks, obtained by means of crosslinking of suitably functionalized macro monomers, and these macro monomers preferably comprise segments derived from caprolactone, glycolide, lactide and/or dioxanone.

The semi-crystalline thermoset materials preferably comprise a component, derived from a macro monomer of caprolactone and glycolide. The amorphous networks comprise components, derived from macro monomers of lactide and glycolide, caprolactone and lactide or lactide and dioxanone. The network structures may furthermore comprise additional functional network components, wherein these additional components are preferably selected among acrylates and methacrylates, preferably butylacrylate.

The number average of the molecular weight of these segments also in connection with the thermoset materials is in the range of from 1000 to 10000 g/mol, in particular 3000 to 10000 g/mol. If more than one monomer unit is present in the segment, for example lactide and glycolide units or caprolactone and glycolide units, the respective content is not restricted. Preferably, however, glycolide, in these cases, is present in an amount of from more than 0 to 30 mol %, preferably from 10 to 20 mol %.

If an acrylate monomer is added during crosslinking, this acrylate monomer preferably is present in an amount of up to 60 wt. %, in particular 25 to 55 wt. %.

The above-mentioned materials typically enable the triggering of the shape memory effect by means of a temperature stimulus, but the SMP materials may be designed in a manner that they can be controlled by means of a different stimulus, such as magnetic fields, ultra sonic, light, electricity or other stimuli.

The above-mentioned polymer materials are in particular suitable as matrix material for drug release systems. The preferred matrix materials are biodegradable, so that in particular in relation to the drug release within the body a second surgical process for the removal of the matrix after drug release is not required. Furthermore, the matrix materials to be used in accordance with the present invention do show a degradation behaviour, which is not associated with a drastic decrease of the mechanical properties of the matrix materials. Furthermore, the matrix materials to be used in accordance with the present invention are polymers showing shape memory properties.

The term polymers showing shape memory properties which is used in the present invention designates materials which may be transferred from a predefined permanent shape into a temporary shape (using suitable shaping methods) and which, after application of an external stimulus, revert to the permanent form. Deformation and fixation of the temporary shape is designated programming. The transformation from the temporary to the permanent shape is designated recovery. The initiation of the recovery is achieved typically, for the matrix materials employed in the present invention, by means of thermal stimulation.

The shape memory properties of the matrix materials used in the present invention enable on the one hand that, for drug release systems which are to be implanted, that a temporary shape may be fixed, enabling minimal invasive procedures. After application at the desired target a shape memory effect may be triggered by means of a suitable stimulation, typically a temperature increase due to the body temperature. This shape memory effect can furthermore be employed in order to release the drug contained in the drug release system. In this connection various embodiments may be realized.

On the one hand the shape memory effect may effect a change in the phase structure, in the pore structure, the surface structure or the crystallinity, which enables a slow and steady (even) release of the drug. Such matrix systems may however comprise optional additional layers, for example the matrix loaded with the drug may be coated with a layer of a non-SMP material (core-shell systems). This additional material can for example enable the secure implantation of the drug release system, for example by means of a suitable surface design. This coating layer may be biodegradable, so that after application at the desired site of action the coating is degraded in order to enable the desired release by means of the SMP material. As an alternative, the additional coating itself may comprise drugs (active agents), which are released prior to the release of the drugs contained in the SMP matrix. In this respect a combination therapy using a time dependent harmonized order of release is made possible. A further possibility of the use of an additional coating is given in cases when the SMP material shows a very rapid release after triggering the shape memory effect and already a noticeable release prior to the triggering of the shape memory effect. The additional coating then prevents the undesired release of the drug prior to the triggering of the shape memory effect. This shape memory effect can then be triggered upon demand, whereby for example the shape memory effect is used in order to destroy the outer coating in order to enable the rapid desired release.

Furthermore the release in matrix systems may be controlled either by diffusion (crystallinity of the matrix), by degradation (degradation of the matrix releases the drug) or a combination thereof. For example a matrix may comprise different domains, of which at least one shows a desired change of the coefficient of diffusion, the melting temperature or the glass transition temperature, so that a control of the release is enabled. A further option of the control of the rate of release from a matrix loaded with a drug is the suitable selection of the compatibility of drug and matrix material (SMP material). A good compatibility per se leads to a slower release, compared with a system showing a low degree of compatibility between drug and matrix material. For example the increase of the hydrophobic content (or the amorphous content) of a network leads to a slower release of hydrophobic drugs. Such an increase of the hydrophobic content of a network (or of a thermoplastic material) can be achieved by means of introduction of butylacrylate segments. In particular with drug release systems comprising drugs such as ethacridine lactate, the increase of the content of glycolate within the matrix, reducing the crystallinity, shows an accelerating effect with respect to the drug release. By means of suitable selection of the respective content of the components a desired drug release can be achieved.

Such matrix systems may be prepared in many different embodiments, which can be designated in a simplified classification as 3D, 2D or 1D systems, such as beads or box-shaped or cylindrical implants (3D), films or foils, stretched or unstretched (2D) or threads or filaments (1D). Such matrix systems furthermore can be assembled in order to provide interesting complex systems. For example matrix films may be assembled with films not comprising a drug to multi-layer laminates in order to enable a further control of the drug release. Such laminate systems preferably comprise n films of SMP material loaded with a drug and alternating layers (n+1) of films of a material not loaded with a drug, which may be prepared from a SMP material or a non-SMP material. This principle is also applicable to other matrix systems of the 1D or 3D type. For example a 3D or 1D system, loaded with a drug, may be coated with a further layer of a SMP material, without drug, for example in order to control the release rate.

The loading of the drugs into such matrix systems can be achieved in different ways, independent from the employed drug and the employed SMP material. Suitable methods comprise (a) the combined dissolution of drug and SMP material in a solvent and subsequent drying (alternatively it is possible to precipitate using a non-solvent for both compounds), (b) the mixing of drug and a precursor material for the SMP material, followed by crosslinking of the precursor material (optionally the mixing is carried out with the aid of a solvent which will then be removed), or (c) swelling of objects made from SMP materials in a solution of the drug. Further possibilities for introducing the drug into a matrix are melt mixing (using an extruder), the chemical fixation of the drug onto the matrix molecules or other similar procedures.

On the other hand, it is also possible to employ the shape memory effect in drug release systems of the second principle type. In this respect it also can be achieved that an enclosed drug is released over a short period of time, which is desired in some fields of application. In this respect, the matrix material of the drug release system in accordance with the present invention may have the function of a membrane, which, after initiating the shape memory effect, is completely permeable with respect to the enclosed drug, so that an immediate release becomes possible. Such drug release systems may either be prepared completely of an SMP material, for example in the form of a hollow body which encloses a depot of the drug, or the system consists of a depot system for the drug having an opening, which is closed with the SMP material.

The first alternative is in particular suitable for encapsulating systems, for example for drugs which are to be employed topically. In the field of cosmetic preparations, active agents, such as vitamins, skin care agents or other agents, which are for example susceptible to oxidation, are encapsulated, so that after the application onto the skin, due to the influence of the body temperature, a shape memory effect is initiated liberating the enclosed drugs. Other possible fields of application are reservoirs for artificial tears or medicaments for topical application which are encapsulated.

In this respect, the shape memory effect of the drug release systems in accordance with the present invention, in particular with drug release systems which are applied topically, can be used in order to liberate the enclosed drug in a controlled manner. Examples of these embodiments of the drug release systems in accordance with the present invention are capsules for skin care agents or capsules for active agents which are applied intra aural, intra nasal or mucosal. In these applications the capsules, constituting the drug release systems in accordance with the present invention, are formulated in the usual manner for drugs which are to be applied topically. One example thereof is a skin cream containing skin care substances enclosed within a drug release system in accordance with the present invention. This offers the advantage, in particular for formulations which have to be applied over a long period of time, that an impairment of the drugs, for example due to oxygen in the surrounding air, can be avoided or at least restricted. After the usual application the desired release of the drug can occur, for example due to the initiation of a temperature induced shape memory effect after application of the formulation (for example application of a skin cream on to skin, whereby the drug is liberated due to a thermally induced shape memory effect, after the drug release system has been present for some time on the skin so that a warming to a temperature near body temperature has occurred).

The drugs to be enclosed within the drug release system in accordance with the present invention may be selected among a broad variety of drugs. The term drug in this respect comprises medicaments as well as other active agents, such as skin care agents, artificial tears, odours, substances required for diagnostic applications, such as contrast agents or radioactive labels, etc. Preferred drugs comprise hormones, antibiotics, enzymes, cancer agents, peptides, anaesthetics, psychopharmaca, analgesics, antiseptics, antimycotic agents, antihistaminic agents, antiviral agents and growth factors. Drugs which have already been successfully employed in release systems with SMP materials comprise ethacridine lactate, enoxacine, nitrofuantoine and gentamicine.

Such drugs can be encapsulated without problems with the polymeric materials employed in accordance with the present invention. Drug release systems wherein the polymeric material serves as the matrix material enable the incorporation of the drugs by means of usual procedures. With thermoplastic materials, the drugs may be incorporated by means of dispersion of the drugs in a polymer solution, followed by drying. Subsequently, the dried mixture can be subjected to a programming step, in order to achieve the desired shape memory properties for the liberation of the incorporated drug. Optionally, further processing steps may occur, for example steps for reducing particle sizes, steps for formulating the drug release system, wherein however the steps have to be conducted in such a manner that an undesired initiation of the shape memory effect is prevented. The thermoset materials to be used in accordance with the present invention can be loaded with drugs, either by means of swelling in a solution of the drug or by means of a method wherein the soluble precursor materials of the thermoset materials are present together with the drug in a solution, wherein due to the subsequent removal of the solvent and the following crosslinking a loaded thermoset material is obtained. As an alternative it is possible to prepare a mixture of prepolymer and drug without solvent, so that the drug is then present in dispersed form in the polymerizable mixture. Following these steps a desired programming may occur, followed again by further optional processing steps.

Concerning the introduction of a drug into a drug release system in accordance with the present invention, the following principle cases can be defined:
1. The drug may be of low molecular weight or the drug may be of high molecular weight.
2. The drug may be hydrophilic (polar) or may be hydrophobic (unpolar).

For these principle cases the following general rules may be given concerning the loading with the drug.

Low Molecular Weight Hydrophilic Drug (e.g. Ethacridine Lactate)

Swelling of networks within a suitable solution of drug (hydrophilic solvents such as propanol or ethylacetate in order to dissolve the drug), followed by drying (loading typically in the range of from 0.1 to about 2 wt. %).

Crosslinking of prepolymers in the presence of drugs (as alternative dissolved in a suitable solvent system or dispersed in the polymerizable mixture). Such a method for introducing a drug is in particular suitable for hydrophilic drugs, since the following processing steps employing hydrophobic solvents do not impair the loading with drugs (loading typically up to 6 wt. %).

Low Molecular Weight Hydrophobic Drug (e.g. Enoxacine, Nitrofurantoine)

Swelling of networks in a solution of a suitable drug (rather hydrophobic solvents, such as dioxane, trichloromethane, but also ethyl acetate, in order to dissolve the drug) and subsequent drying (loadings of typically 0.1 to about 2 wt.- %).

Crosslinking of prepolmers in the presence of drug (either dissolved in a suitable solvent system or dispersed within a polymerizable mixture) (loadings typically up to 6 wt.- %).

High Molecular Weight Drug

High molecular weight drugs, such as proteins, may also be incorporated into drug release systems in accordance with the present invention. However, there often is encountered the problem that high molecular weight drugs cannot be incorporated into the networks in satisfactory amounts by means of swelling methods and that furthermore the typical processing steps of thermoplastic systems lead to thermal or mechanical stresses which are detrimental for high molecular weight drugs. Therefore it is preferred to encapsulate such high molecular weight previously for protection/stabilization, for example into PEG microparticles, or to protect/stabilize the drug by means of interaction with a polyelectrolyte, prior to its incorporation into a matrix. The incorporation then preferably occurs by means of network generation in the presence of the drug by crosslinking prepolymers or by traditional methods for the processing of thermoplastic materials, such as extrusion.

Surprisingly it has been found that the delicate materials, which are employed in the present invention as matrix materials for drug release systems, are substantially not affected with respect to their thermal or mechanical properties due to the incorporation of the drugs. The trigger temperature for example (temperature at which the shape memory effect is initiated) is not changed due to drug incorporation into the drug release systems, or only to a minor extent, compared with the unloaded drug release systems. Mechanical properties, such as E modulus are also not affected, or only to a minor extent. Therefore the loaded drug release systems are able to display shape memory effects for drug release, despite the loading with the drug. However, for some systems a minor variation of the $T_g$ or $T_m$ can be detected, which may be explained by a softening effect displayed by the low molecular weight drugs contained or the (partial) suppression of crystallization. Such effects however occur to a noticeable extent only with homonetworks, i.e. networks on the basis of caprolactone and in particular when the incorporation of the drug was carried out by network preparation in the presence of dispersed drug with rather short segment lengths of the employed prepolymers. With AB-networks such effects are rather not given, so that a change of the structure of the network can suppress the variation of the thermal properties.

In summary it therefore can be stated that an interesting and versatile system is provided, which can be adapted to the respective requirements of a given application profile.

A further option is that the above mentioned polymers having shape memory properties, described above as matrix materials, coat a depot of a drug, so that the drug is not incorporated (or only to a minor extent) within the shape memory polymer. Such encapsulating systems are in particular of advantage when the compatability between drug and shape memory polymer is rather low. Such encapsulating systems may be prepared in a usual manner. In view of the fact that the shape memory polymers are used in this embodiment as encapsulating materials, it is possible to employ the shape memory effect, by carefully selecting the shape memory polymer, for the control of the drug releasing properties. It is for example possible to select a material which is, after triggering the shape memory effect, completely permeable for the encapsulated drug, so that a rapid release is made possible. On the other hand is it also possible to select a material which enables only a slow release of the drug, after triggering the shape memory effect, so that such an embodiment enables a long term, controlled drug release.

It is however of course also possible to use the shape memory effect of the drug release systems of the present invention not for the drug release but for enabling the placement of implants by minimal invasive techniques. In view of the fact that the preferred polymers to be used in accordance with the present invention are biodegradable, a rather even drug release, in particular for the matrix type drug release systems, is made possible due to the slow degradation within a biological system. In view of the fact that the drug release systems show a degradation behaviour which is free of detrimental effects, such as a burst effect, the drug release systems of the present invention of this embodiment enable a controlled release of the drug even without using the shape memory effect.

In view of the possibility of employing the SMP materials for unlimited types of applications, and in view of the above described possibilities of varying the disclosed embodiments, it is readily apparent that the possible applications of the drug release systems of the present invention cover a broad range.

The drug release systems may for example be part of implants. This is possible either due to a (partial) coating provided on the implant, or by incorporating a suitable shape memory polymer for drug release into the implant itself. Examples are stents, artificial joints, artificial vessels, sutures, chirurgical devices, such as a clip, a catheter, a needle of a syringe, etc. In particular stents, sutures or artificial vessels may comprise themselves the SMP material, whereas the other exemplary devices preferable are coated, in total or partially. Such embodiments offer the possibility that the implants or the other devices serve, in addition to their original function, also as drug release system. This offers great advantages since the required drugs may be provided directly from the implant or any of the other devices. A prosthesis for example may comprise a coating releasing drugs reducing repulsion reactions or inflammation. Sutures may also release anti-inflammatory drugs, whereas stents may contain drugs which inhibit blood coagulation or growth of cells onto the stent.

A further option is the use of the drug release systems in accordance with the present invention in the form of particles, for example in the form of micro or nano-particles (matrix-type system) or in the form of micro or nano-capsules. Such particles are valuable in a broad range of applications, some of which are presented in the following.

Microparticles are in particular suitable of applications in eyes, either only as drug carrier or with a further function. Such microparticles may for example be used for a temporary closure of the lachrymal canal, which is required for some types of therapy. In this canal the drug is then released. After a desired period of time the lachrymal canal will then be opened up. The microparticles furthermore may be employed as drug carriers or for occlusion therapy within blood vessels.

Particles in accordance with the present invention may also be employed in aerosols, for pulmonary drug release. Finally it is possible to employ the particles in the field of tissue engineering, in order to liberate bioactive substances on demand from the carrier supporting the tissue.

The drug release systems in accordance with the present invention may also be employed for transdermal applications, such as plasters. Due to the shape memory effect the diffusion coefficient may be influenced in such systems, in order to control transdermal drug delivery, for example by increasing the rate of release of the drug.

A further option are oral application forms, with which a control of the release is possible within the stomach or the intestine. A further option in this respect is the use of the aforementioned drug pump systems.

In the following preferred polymers, to be used in accordance with the present invention are described.

Networks

Covalent polymer networks made from oligo-epsilon-hydroxycaproate dimethacrylates and butyl acrylate are shape memory polymers which have been proved as being degradable in vivo and compatible with cells. By a suitable selection of the molecular parameters of the polymer system, properties such as melting temperature, crystallinity, hydrolytic degradation behaviour and hydrophilic property of the material may be adjusted. The networks are prepared photochemically after a suitable functionalization of the terminals of the macromers, in order to obtain dimethacrylates. In order to control the rate of degradation easily hydrolysable ester bonds are incorporated into the macrodimethacrylates. In order to achieve this epsilon-caprolactone is copolymerised with diglycolide. The comonomer ratio of the macrodimethacrylates is varied, so that a crystallization of glycolate segments can b inhibited, so that melting temperature and crystallinity depend only from the oligo-epsilon-caprolactone segments. The synthesis of the co-oligo(ester)diols, based on epsilon-caprolactone and diglycolide is initiated by ethylene glycol and catalysed by dibutyl tin (IV) oxide in melt phase by ring opening polymerisation (see below)

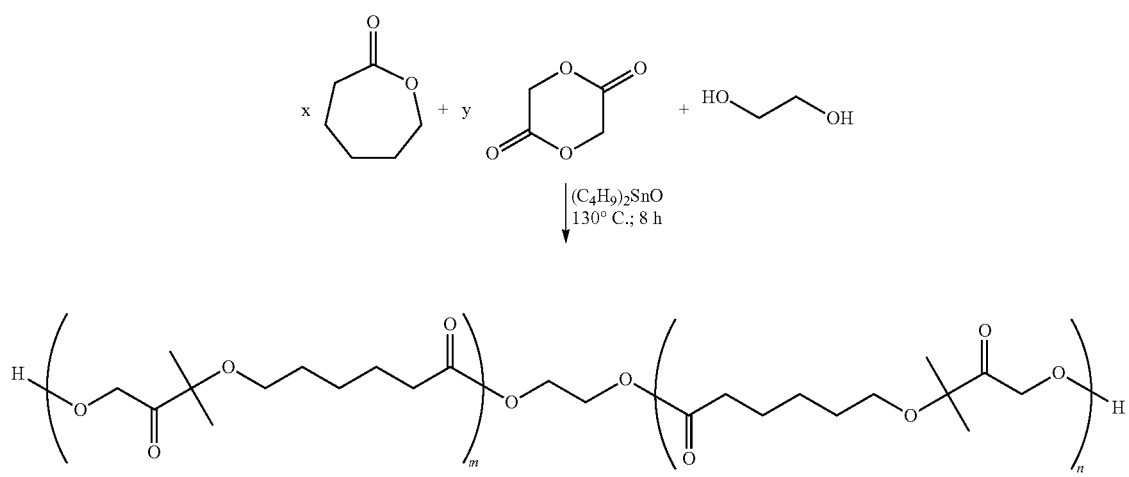

Using the esterification catalyst dibutyl tin (IV) oxide a statistical distribution of the repeating units is obtained in the cooligomer, using a copolymerization duration of 8 h. Functionalization of the terminals of the oligo[(ϵ-hydroxycaproate)-co-glycolate]diols is achieved by a stochiometric reaction of the terminal hydroxy group with methacryloyl chloride using triethyl amine as base (see below).

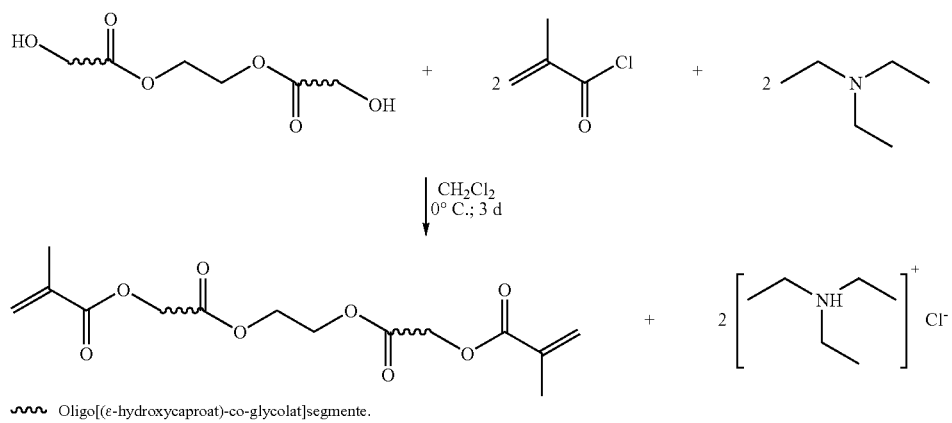

Oligo[(ε-hydroxycaproat)-co-glycolat]segmente.

The prepolymers are crosslinked in the melt without the aid of a photocatalyst by photoinitiation at 70° C. If AB networks are desired butyl acrylate is crosslinked with the oligo[(ε-hydroxycaproate)-co-glycolate]dimethacrylates. Using $^{13}C$-NMR on swollen AB-networks it was shown that the content of butyl acrylate within the network can be controlled with the respective content in the polymerization mixture. Concerning the networks it has to be differentiated between networks prepared from macrodimethacrylates and AB-networks, which are composed of macrodimethacrylates and the comonomer butyl acrylate.

The crosslinking points of the networks are formed from the reacting terminal methacrylate groups of the prepolymers. These are designated as multifunctional crosslinking points, since the length of the thereby generated oligo(methacrylate)sequences, in relation to the segment length of the co-oligoesters, has to be considered as being much shorter. The excess of butyl acrylate in relation to the amount of oligo(ester)units within the AB-networks leads, due to the reaction of the terminal dimethacrylate groups with butyl acrylate, in addition to multifunctional crosslinking points, to mainly trifunctional crosslinking points.

The melting temperature $T_m$ of a system determines the triggering or switching temperature $T_{trans}$, at which, i.e. when the temperatures increases above it, the shape memory effect is initiated and the permanent shape is recovered. In contrast to the thermoplastic materials polymer networks are able to recover the permanent shape almost completely, since viscoelastic effects, which lead to irreversible deformation, are suppressed due to the covalent crosslinking.

By introducing glycolide as comonomer unit into the prepolymers, up to a content of 30 mol-%, the melting temperature and accordingly $T_{trans}$ of the network can be adjusted to a value of between 20° C. and 57° C. Polymerization of the macrodimethacrylates in the presence of butyl acrylate yields a decrease of the crystallinity of the materials, which is determined exclusively by the crystalline oligo(ε-hydroxycaproate)segments. Adjusting the comonomer ratio allows the adjustment of th modulus of elasticity of the networks to the range of between 0.4 MPa and 64 MPa.

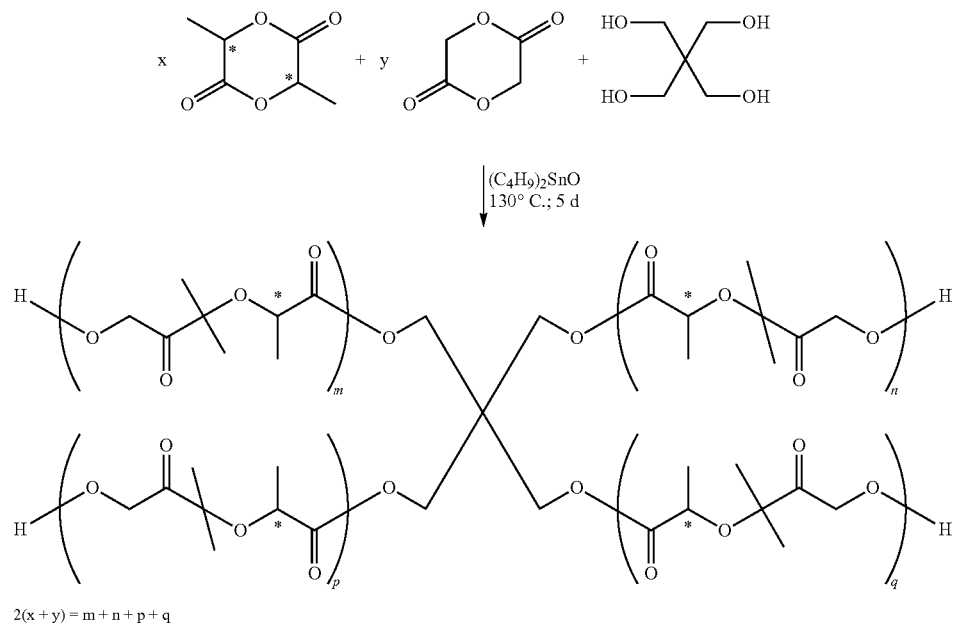

Amorphous copoly(esterurethane)networks of oligo[(rac-lactate)-co-glycolate]tetroles and diisocyanate offer also the advantage of a hydrolytically degradable polymer matrix having shape memory properties. Copolymers and cooligomers, respectively, made of rac-dilactide and diglycolide enable by varying the comonomer ratio to adjust the properties in relation to glass transition temperature and rate of hydrolytic degradation. Synthesis of the polymer networks occurs by polyadition using tetrafunctional hydroxytelechelic cooligo(esters) using an aliphatic diisocyanate.

Tetrafunctional cooligomers prepared from rac-dilactide and diglycolide are obtained by ring opening polymerization in the melt. Initiation is achieved by pentaerythrite in the presence of dibutyl tin (IV) oxide (see below).

Since it has been shown for the copolymerization of L,L-dilactide and diglycolide that dibutyl tin (IV) oxide acts as esterification catalyst, a statistical distribution of the repeating units is expected during the preparation of the macrotetroles. Preparation of the copoly(esterurethane)networks is achieved by coupling the tetrafunctional telecheles with TMDI (see below).

Scheme 1: schematical representation of network architecture

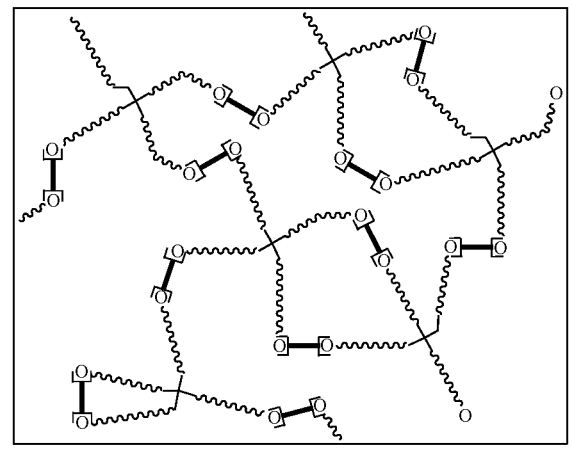

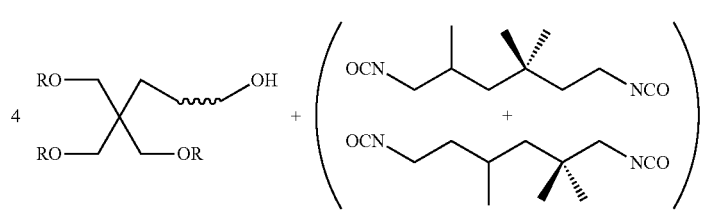

↓ 70° C., 3 d

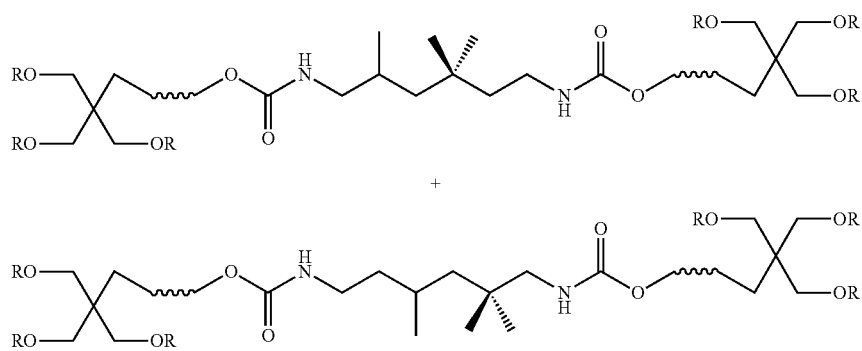

R and ∿∿∿ respectively are oligo[(rac-lactate)- co-glycolate]segments

For obtaining a quantitative coupling of the star shaped hydroxytelecheles and to inhibit side reactions such as dimerization and trimerization of the diisocanates or formation of allophanates, TMDI has to be employed in equimolar amounts. The expected network architecture is shown schematically in scheme 1.

-continued

∿∿∿ oligo[rac-lactat)-co-glycolate]segments tetrafunctional crosslinking point

O—■—O  diurethane unit

By using tetrafunctional prepolymers, under the condition that polydispersity is kept low, an almost regular network is expected to be formed having defined network points (crosslinking points). Accordingly networks obtained via this synthesis route are designated model-networks. Only the intramolecular coupling of two terminals of one oligomer or non reacted terminals (dangling chains) due to non quantitative reaction, may be the reason and source of irregularities.

The use of the above mentioned initiators, such as ethylene glycol, pentaerythrite but also 1,1,1-tris(hydroxymethyl) ethane enables the formation of multifunctional macromonomers, i.e. linear, three terminals, or four terminals containing hydroxy telechelic macromonomers.

Additional networks which may be prepared in a similar manner comprise copolyestersegments on the basis of lactide and caprolactone or lactide and dioxanone, which can be prepared as described above. The content of dioxanone or caprolactone, respectively, preferably amounts to 5 to 70 mol % or 3 to 45 mol %, respectively, in particular 10 to 50 mol % or 10 to 30 mol %, respectively. The number average molecular weight of the segments (macromonomers) is as defined above. Also in this embodiment it is possible to copolymerize acrylate monomers.

A further system which may be employed in accordance with the present invention is a copolyester on the basis of an oligopropylene glycol, having a number average molecular weight of from 1000 to 6000 g/mol, comprising units on the basis of glycolide and lactide, so that the macromonomer has a number average molecular weight of about 2000 to 15000 g/mol.

Further preferred networks, which may be employed in accordance with the present invention are interpenetrating networks.

Preferred interpenetrating networks (IPN) are networks which comprise, in addition to the domains of switching segments of oligo[(rac-lactate)-co-glycolate] a at room temperature rubber elastic phase of crosslinked poly(acrylate)s. The networks on the basis of poly(acrylate) are obtained by radical polymerisation of low molecular weight acrylates, admixed with a dimethacrylate as crosslinking agent. The monomers are introduced by means of swelling of the networks obtained from oligo[(rac-lactate)-co-glycolate]tetroles and a diisocyanate in a solution of the dimethacrylate and the liquid acrylates. The acrylates introduced by this swelling procedure may be polymerized subsequently by photochemical reactions. An advantage of this procedure of preparation is the fact that defined, already prepared networks with oligo[(rac-lactate)-co-glycolate]segments are employed. Possible variations of the thermal or mechanical properties can therefore be directly linked to the formation of the poly(acrylate) network. During the preparation of a sequential IPN by means of introduction of low molecular monomers into the already formed network it is possible to include monomers having functional groups, such as hydroxy functionalities.

These polymer systems are based on networks, which are formed by coupling of oligo[(rac-lactate)-co-glycolate]tetroles, having a content of glycolate as defined above, with a number average molecular weight as defined above, using TMDI. As poly(acrylate) component poly(ethyl acrylate), poly(butyl acrylate) and poly(hexyl acrylate) are preferred, which are suitable for the generation of a rubber elastic phase due to their low glass transition temperatures. Poly(ethyl acrylate) for example shows an average value of $T_g$ of $-24°$ C. For poly(butyl acrylate) and poly(hexyl acrylate) the glass transition temperatures are about $-55°$ C and $-57°$ C. respectively. These materials may be rendered more hydrophilic by using (2-hydroxy ethyl)acrylate as monomer. Poly(hydroxy ethyl acrylate) shows, in dry state, a glass transition temperature of from 35° C. to 58° C. As cross linking agent during the radical polymerisation an oligo(propylene glycol) dimethacrylate (M-PPG-560) having a number average molecular weight, according to the information of the producer, of 560 g·mol$^{-1}$ may be used. The hydrophilicity of the materials has a high relevance for potential applications of biodegradable shape memory polymers in the medical field. The hydrophilicity influences for example the release properties of drugs from a polymer matrix or the interaction of cells with the surface of the implant. Using (2-hydroxy ethyl) acrylate aims at regulating the hydrophilicty and the water absorption of the IPN by varying the content of poly(acrylate)s within the network.

The content of acrylate within the network preferably is within the range of from 10 to 80 wt.-%, based on the overall composition, more preferably within the range of from 15 to 75 wt.-% and in particular in the range of from 20 to 60 wt.-%.

The following examples illustrate the present invention further.

EXAMPLES

Thermoplastic materials comprising polyester segments of caprolactone were loaded with the drugs gentamicin and enoxacin, respectively, with drug loadings from 1 to 20 wt.-%. Thereafter the melting point of the caprolactone segments was determined. In comparison with the matrix polymer not loaded with drug (loading occurred through mixing in solution followed by drying) an only insignificant variation of the melting point was determined.

The above mentioned samples were further evaluated with respect to their mechanical properties. In particular the E modulus was determined. This modulus increases, in comparison to the matrix polymers not loaded with drug, slightly in the drug containing samples.

Further, polyester methacrylate networks with polyester segments of caprolactone and glycolide were loaded with nitrofurantoin, enoxacin and ethacridinlactate (1 to 2 wt.-%) (swelling method) and the E modulus was determined. In comparison with the materials not containing a drug, it was shown that the loading with the drug does not alter significantly the E modulus.

Furthermore drug release tests were carried out with biodegradable matrix polymers. The above mentioned polyester methacrylate networks were loaded with 5% gentamicin and enoxazin, respectively. Samples having a size of 1×2 cm$^2$ were cut open and placed into a medium for release (4 ml phosphate buffer, pH 7). The pieces of the films were placed in tubes for a centrifuge, in a manner allowing the buffer solution to contact the films from all sides. The centrifuge tubes were placed into a shaking water bath at 37° C. and at predetermined intervals the medium for release was exchanged completely in order to determine the amount of the drug released.

These experiments were carried out with networks on the basis of paradioxanone and polylactide-co-glycolide. A substantially linear rate of release of the drugs was found, without occurrence of undesired burst effects.

This experiment was also conducted with the drug gentamicin using a thermoset material on the basis of paradioxanone and caprolactone. It was found that at the beginning of the release a rapid release (burst-effect) occurred, whereafter a plateau was reached within two days.

This release system was modified by dip coating into the matrix polymer. Furthermore a laminate system was prepared, comprising a drug containing film, laminated on both sides with polymer.

These drug release systems displayed a different release profile. Here the release occurred, as described above for the systems on the basis of paradioxanone and polylactide-co-glycolide, substantially linear over a period of several weeks.

The above described laminate systems may comprise one drug containing film layer or several drug containing film layers, each sandwiched between films of pure polymer. Release experiments were also conducted with networks on the basis of polylactide-co-glycolide (number average molecular weight of segments about 10000, 15 wt.-% glycolide content), comprising ethacridinlactate. This experiment likewise displayed a substantially linear release, with a slightly accelerated release at the beginning.

Loading of Thermoplastic Materials

Loading was achieved by means of dispersing the drugs in the solution of polymer (in chlorinated solvents) followed by drying. The dried mixture is pressed between teflon foils and melted for film formation. The used drugs may be hydrophilic as well as lipophilic. As hydrophilic model substance gentamicin isused, whereas enoxacin is used as lipophilic model substance. Drug contents of up to 20 wt % can be achieved.

Loading of Networks by Swelling

The loading of drugs into polymer networks (present in the form of thin films, with a weight of about 60 mg) is achieved by means of swelling in a 100-fold excess (V/m) of drug solution within a predetermined period of time. Usually the swelling time is 24 h (a saturation of the drug loading is however already achieved after about 1.5 h). Saturated solutions of enoxacin in chloroform or ethyl acetate, of nitrofurantoin in dioxane and of ethacridinlactate in a solvent mixture of equal parts (weight) of chloroform or ethyl acetate, and 2-propanol are used in this respect. Thereafter the swollen materials are withdrawn from the solutions. The polymer networks are dried at 60° C. in a vacuum (1 mbar). In Table 1 the networks, loaded with drug by means of swelling are shown, in relation to the saturated drug solutions employed.

TABLE 1

Examples of drug loading in polymer networks by swelling in a saturated solution of the drug

| Example | Network | Saturated solution of drug |
|---|---|---|
| 1 | N-CG(14)-3 | Enoxacin-Ethylacetate |
| 2 | N-CG(14)-3 | Ethacridinlactate-Ethylacetate/2-Propanol (1:1 w/w) |
| 3 | N-CG(14)-5 | Enoxacin-Ethylacetate |
| 4 | N-CG(14)-5 | Ethacridinlactate-Ethylacetate/2-Propanol (1:1 w/w) |
| 5 | N-CG(14)-7 | Enoxacin-Ethylacetate |
| 6 | N-CG(14)-7 | Ethacridinlactate-Ethylacetate/2-Propanol (1:1 w/w) |
| 7 | N-CG(14)-10 | Enoxacin-Ethylacetaet |
| 8 | N-CG(14)-10 | Enoxacin-Chloroform |
| 9 | N-CG(14)-10 | Nitrofurantoin-Dioxan |
| 10 | N-CG(14)-10 | Ethacridinlactate-Ethylacetate/2-Propanol (1:1 w/w) |
| 11 | N-CG(14)-10 | Ethacridinlactate-Chloroform/2-Propanol (1:1 w/w) |
| 12 | N-CG(0)-10 | Enoxacin-Ethylacetate |
| 13 | N-CG(0)-10 | Ethacridinlactate-Ethylacetate/2-Propanol (1:1 w/w) |
| 14 | N-CG(12)-10 | Enoxacin-Ethylacetate |
| 15 | N-CG(12)-10 | Ethacridinlactate-Ethylacetate/2-Propanol (1:1 w/w) |
| 16 | N-CG(21)-10 | Enoxacin-Ethylacetate |
| 17 | N-CG(21)-10 | Ethacridinlactate-Ethylacetate/2-Propanol (1:1 w/w) |
| 18 | N-CG(30)-10 | Enoxacin-Ethylacetate |
| 19 | N-CG(30)-10 | Ethacridinlactate-Ethylacetate/2-Propanol (1:1 w/w) |
| 20 | AB-CG(0)-10 | Enoxacin-Ethylacetate |
| 21 | AB-CG(0)-10 | Ethacridinlactate-Ethylacetate/2-Propanol (1:1) |
| 22 | AB-CG(12)-10 | Enoxacin-Ethylacetate |
| 23 | AB-CG(12)-10 | Ethacridinlactate-Ethylacetate/2-Propanol (1:1) |
| 24 | AB-CG(14)-10 | Enoxacin-Ethylacetate |
| 25 | AB-CG(14)-10 | Ethacridinlactate-Ethylacetate/2-Propanol (1:1) |
| 26 | AB-CG(21)-10 | Enoxacin-Ethylacetate |
| 27 | AB-CG(21)-10 | Ethacridinlactate-Ethylacetate/2-Propanol (1:1) |
| 28 | N-CG(14)TOH-5 | Enoxacin-Ethylacetate |
| 29 | N-CG(14)TOH-5 | Ethacridinlactate-Ethylacetate/2-Propanol (1:1) |
| 30 | N-LG(18)-10 | Enoxacin-Chloroform |
| 31 | N-LG(18)-10 | Nitrofurantoin-Dioxan |
| 32 | N-LG(18)-10 | Ethacridinlactate-Chloroform/2-Propanol (1:1 w/w) |

N-CG = network on the basis of caprolactone-co-glycolide segments

AB-CG-10 = AB network of caprolactone-co-glycolide segments, Copolymer n-butyl acrylate N-CG(14)TOH-5 = copolyester urethane network of oligo[(ε-hydroxycaproate]-co-glycolate]tetraol and diisocyanate N-LG(18)-10 = copolyester urethane network of oligo[(rac-lactate)-co-glycolate]tetraol and diisocyanate Numbers in brackets designate the molar content of glycolate, in relation to the used macromonomer, the other numbers designate $M_n$ for the used macromonomers, in 1000 g/mol (5 = 5000 g/mol)

Table 2 shows some examples of the drug content of some networks—loaded by a swelling procedure—determined by various methods.

TABLE 2

Drug content of some networks. $\mu_{WS}$ is the drug content in the matrix based on the total mass, Q is the degree of swelling in the drug containing solution, $k_v$ is the coefficient of distribution and $\delta$ is the solubility parameter of the drug.

| Network/drug | $\mu_{WS}$(1) Wt.-% | $\mu_{WS}$(2) Wt.-% | $\mu_{WS}$(3) Wt.-% | Q Vol.-% | $k_v$ — | $\delta$ MPa$^{1/2}$ |
|---|---|---|---|---|---|---|
| N-CG(14)-10/Enoxacin+ | 0.72 | | | 930 ± 60 | 0.33 | 29.1 |
| N-CG(14)-10/Nitrofurantoin | 1.65 | 2.2 | 2.7 | 910 ± 80 | 0.63 | 31.7 |
| N-CG(14)-10/Ethacridinlactate | 0.60 | 0.5 | 1.6 | 530 ± 10 | 0.47 | 28.6 |
| N-LG(18)/Enoxacin | 2.56 | | | 740 ± 20 | 2.35 | 28.08 |
| N-LG(18)/Nitrofurantoin | 1.40 | | | 790 ± 10 | 0.50 | 31.73 |
| N-LG(18)/Ethacridinlactate | 1.49 | | | 390 ± 10 | 1.43 | 27.62 |

(1) UV/VIS-spectroscopical determination of drug content after methanolysis of the network
(2) Determination of the content on the basis of the increase of the mass of the network after loading
(3) Determination of the content, calculated on the basis of the decrease of the concentration of the drug in the solution Loading of networks in situ and crosslinking First a solution (10%, (m/V)) of the prepoymers (dimethacrylates) in a solvent mixture of equal parts (weight) of dichloromethane and 2-propanol was prepared. A content of between 0.2 wt.-% and 6.6 wt.-% ethacridinlactate (based on the total weight of the drug containing matrix) was added. This solution was reduced in volume at 50° C, followed by drying at 70° C. for about 2 h in a vacuum (1 mbar). Starting from this two component mixture crosslinking is carried out as described below.

Photochemical crosslinking of the macrodimethacrylates was carried out between two glass plates using a Heraeus Noble Light Excimer Laborsystem (308 nm). The glass mould is fixed in a distance of 7.5 cm on a temperature controlled heating plate at 70° C.±2° C. below the UV tubes. The heat transfer from heating plate to glass plate is guaranteed by a block of metal. The duration of irradiation of the samples is 30 min for networks N-CG and 60 min for the AB networks AB-CG.

TABLE 3

Designation, composition, and swelling behaviour of networks obtained by in situ incorporation of Ethacridinlactate. Molar content of glycolate $\chi_G$ and number average molecular weight $M_n$ of the used macrodimethacrylates as determined by $^1$H-NMR-Spektroskopie; weight content of drug $\mu_{WS}$ based on total weight. Q is the degree of swelling in CHCl$_3$ and G is the gel content

| Network | $\chi_G$ mol-% | $M_n$ g mol$^{-1}$ | $\mu_{WS}$ Mass.-% | Q Vol.-% | G Wt.-% |
|---|---|---|---|---|---|
| N-CG(14)-3-Etha(1)Dsp | 13 | 3500 | 1.0 | 610 ± 10 | 71 |
| N-CG(14)-5-Etha(1)Dsp | 14 | 4900 | 1.0 | 640 ± 40 | 92 |
| N-CG(14)-10-Etha(0,2)Dsp | 14 | 12800 | 0.2 | 900 ± 10 | 84 |
| N-CG(14)-10-Etha(1)Dsp | 14 | 12800 | 1.0 | 980 ± 20 | 85 |
| N-CG(14)-10-Etha(2)Dsp | 14 | 12800 | 2.0 | 1020 ± 110 | 62 |
| N-CG(14)-10-Etha(4)Dsp | 14 | 12800 | 3.9 | 980 ± 40 | 75 |
| N-CG(14)-10-Etha(5)Dsp | 14 | 12800 | 4.8 | 1040 ± 20 | 71 |
| N-CG(14)-10-Etha(6)Dsp | 14 | 12800 | 5.7 | 1080 ± 150 | 53 |
| N-CG(0)-10-Etha(1)Dsp | 0 | 10800 | 1.0 | 850 ± 50 | 93 |
| N-CG(21)-10-Etha(1)Dsp | 21 | 13500 | 1.0 | 1040 ± 20 | 67 |

Hydrolytic Degradation Experiments

The hydrolytic experiments were carried out using planar samples having a size of 10 mm×15 mm and a thickness of about 0.2 mm (poly(esterurethane)networks) and 0.5 mm (photochemically crosslinked polymers), respectively, in centrifuge vessels having a volume of 15 ml and made from polypropylene. The samples were washed, prior to the experiment three times with hexanes and dried in vacuum (1 mbar). Thereafter the weight of each sample is determined ($m_{ini}$). As degradation medium a phosphate buffered aqueous solution of Na$_2$HPO$_4$ (0.1 mol$\mu$L$^{-1}$) and KH$_2$PO$_4$ (0.063 mol $\mu$L$^{-1}$) having a pH of 7.0 is used. The capacity of the buffered solution of a volume of 15 ml is sufficient to buffer 85 mmol acid. In order to avoid growth of microorganisms during the degradation 0.25 g l$^{-1}$ sodium azide are added to the buffered solution. The experiment is carried out without exchanging the degradation medium with a control of the pH value at regular intervals in a temperature controlled shaking water bath at 37° C. or 70° C. with 60 revolutions per minute. The temperature is regulated with an accuracy of ±0.1 K.

The number of samples, degraded separately in one line of experiments corresponds to the number of predetermined measurement intervals. At the respective time the sample is withdrawn from the degradation medium. After dabbing with cellulose the weight of the sample ($m_h$) is determined. Thereafter the sample is dried at 30° C. in a vacuum (1 mbar) and the weight is determined again ($m_{ht}$). On the basis of these measurements the weight ratio $\mu_{rel}$, and the water absorption H in wt.-% during the hydrolytic degradation are determined.

$$\mu_{rel} = \frac{m_{ht}}{m_{ini}} \quad (1)$$

$$H = \frac{m_h - m_{ini}}{m_{ini}} \quad (2)$$

Drug Release Experiments of the Drug Containing Networks

Determination of the drug release from polymer networks was carried out using planar samples of a size of 1 cm×1 cm having a thickness of about 0.2 mm (poly-(esterurethane) networks) and of 0.5 mm (photochemically croslinked polymers), respectively. Samples are placed into polypropylene centrifuge vessels (which may be closed) of a volume of 15 ml and placed into contact with 4 ml of the releasing medium. As releasing medium a phosphate buffered aqueous solution of $Na_2HPO_4$ (0.1 mol $\mu L^{-1}$) and $KH_2PO_4$ (0.063 mol $\mu L^{-1}$) having a pH of 7.0 is used. The release experiment is carried out in a temperature controlled shaking water bath at 37° C. with 60 revolutions per minute. The temperature is controlled with an accuracy of ±0.1 K. By completely exchanging the releasing medium at defined intervals it is possible to secure that a drug concentration of no more than 10% of the saturation concentration is not exceeded (sink conditions). The experiment is concluded when all of the drug has been released. The establishment of the release profile occurs by means of determination of the released drug by UV-Vis-spectroscopy. The resulting release profiles represent the arithmetical average from parallel experiments regarding the release from three samples of one material.

If the experiment is terminated prior to the complete release of the drug from the matrix, a determination of the drug remaining in the polymer network becomes necessary. The matrix is removed from the releasing medium, dabbed with cellulose and dried at 35° C. in a vacuum (1 mbar). Using 5 ml chloroform the networks are swollen, and destroyed mechanically using a glass rod. Using additional 5 ml chloroform the swollen enoxacin containing fragments are extracted. With ethacridinlactate containing networks extraction is carried out using 5 ml 2-propanol. After 2 h the mixture is filtered using a G4 glass fritt and the concentration of drug in the filtrate is determined photometrically. The content of drug remaining in the matrix is added to the content as determined with the release experiment.

The invention claimed is:

1. A drug release system comprising a laminate structure comprising:
    at least one layer comprising a matrix made from a shape memory material and at least one drug dispersed in the matrix; and
    layers from a shape memory material not containing a drug and sandwiching the at least one layer comprising the at least one drug on both surfaces,
    wherein the shape memory material of the layers not containing a drug, after triggering of the shape memory effect, controls the rate of release of the drug.

2. A drug release system comprising:
    at least one drug;
    a reservoir for receiving the at least one drug, and
    at least one of a coating and a membrane closing the reservoir,
    wherein one of a material for the reservoir and a material for the coating or membrane is made from a shape memory material and wherein the shape memory material, after triggering the shape memory effect, controls the rate of release of the drug.

3. The drug release system according to claim 2, wherein the shape memory effect induces a change in shape of the reservoir made from the shape memory material, leading to a change of a permeability of the coating or membrane with respect to the drug.

4. The drug release system according to claim 2, wherein the shape memory effect induces a change in shape of the reservoir made from the shape memory material, the change of shape of the reservoir leading to a destruction of the coating or membrane enabling release of the at least one drug.

5. The drug release system according to claim 2, wherein the shape memory effect induces a change in shape of the coating or membrane made from the shape memory material, leading to a destruction of the coating or membrane enabling release of the at least one drug.

6. The drug release system according to claim 2, wherein the shape memory effect induces a change in one of a permeability, a pore structure, and a crystallinity of the coating or membrane made from the shape memory material, leading to a change in release of the at least one drug.

7. The drug release system according to claim 1, wherein the laminate structure comprises a number of n layers comprising that at least one drug and a number of n+1 alternating layers not containing a drug.

8. The drug release system according claim 1, wherein the drug release system is a minimally invasive implantable device.

9. The drug release system according claim 2, wherein the drug release system is a minimally invasive implantable device.

10. The drug release system according to claim 1, wherein the shape memory effect is triggered by a change in temperature, light, or a combination thereof.

11. The drug release system according to claim 2, wherein the shape memory effect is triggered by a change in temperature, light, or a combination thereof.

* * * * *